(12) United States Patent
Masansky (10) Patent No.: US 10,292,762 B2
(45) Date of Patent: May 21, 2019

(54) ELECTROSURGICAL DEVICE AND ITS USE FOR REMOVING LARGE BLADDER TUMORS

(71) Applicant: Igor Masansky, Los Gatos, CA (US)

(72) Inventor: Igor Masansky, Los Gatos, CA (US)

( * ) Notice: Subject to any disclaimer, the term of this patent is extended or adjusted under 35 U.S.C. 154(b) by 476 days.

(21) Appl. No.: 14/438,488

(22) PCT Filed: Oct. 25, 2012

(86) PCT No.: PCT/IB2012/002145
§ 371 (c)(1),
(2) Date: Apr. 24, 2015

(87) PCT Pub. No.: WO2014/064480
PCT Pub. Date: May 1, 2014

(65) Prior Publication Data
US 2015/0289928 A1    Oct. 15, 2015

(51) Int. Cl.
*A61B 18/14*  (2006.01)
*A61B 18/12*  (2006.01)
(Continued)

(52) U.S. Cl.
CPC ...... *A61B 18/1492* (2013.01); *A61B 17/3205* (2013.01); *A61B 18/1206* (2013.01);
(Continued)

(58) Field of Classification Search
CPC ............ A61B 17/3025; A61B 18/1206; A61B 18/1485; A61B 18/149; A61B 18/1492;
A61B 2017/0019; A61B 2018/00517; A61B 2018/00607; A61B 2018/00708; A61B 2018/00982; A61B 2018/1472
(Continued)

(56) References Cited

U.S. PATENT DOCUMENTS 3,885,569 A * 5/1975 Judson ................... A61B 18/12
606/37
4,517,976 A * 5/1985 Murakoshi ............... A61B 1/05
348/E7.087

(Continued)

OTHER PUBLICATIONS

International Search Report in Application No. PCT/IB12/02145 filed Oct. 25, 2012.

*Primary Examiner* — Michael F Peffley
(74) *Attorney, Agent, or Firm* — IP Spring (57) ABSTRACT

An electrosurgical apparatus having a HF power source providing HF energy for electrosurgery and a circuitry to control application of said HF energy to an electrode end used in electrosurgically operating on a patient is characterized in that said circuitry is adapted to apply in a dissecting mode said HF energy for dissecting to an electrode end automatically in the form of pulses such that the pulses automatically have a defined length. This device can be used for exploration of the bladder and en bloc radical removal of a large tumor using the active resection electrode loop of an optic resectoscope such that the bladder wall layers below the tumor base within the intact tissue margin are prepared using step-by-step coagulation and dissection of the tumor nutrient vessels and of the interlayer tissue fibers performed by impulsive turns-on of the electrosurgical apparatus in-use in the monopolar dissection mode.

6 Claims, 2 Drawing Sheets

(51) Int. Cl.
*A61B 17/3205* (2006.01)
*A61B 17/00* (2006.01)
*A61B 18/00* (2006.01)

(52) U.S. Cl.
CPC ........ *A61B 18/149* (2013.01); *A61B 18/1485* (2013.01); *A61B 2017/0019* (2013.01); *A61B 2018/00517* (2013.01); *A61B 2018/00607* (2013.01); *A61B 2018/00708* (2013.01); *A61B 2018/00982* (2013.01); *A61B 2018/1472* (2013.01)

(58) Field of Classification Search
USPC ...................................... 606/32–50
See application file for complete search history.

(56) References Cited

U.S. PATENT DOCUMENTS

| | | | | |
|---|---|---|---|---|
| 4,532,924 | A | * | 8/1985 | Auth ...................... A61B 18/14 606/50 |
| 5,658,280 | A | * | 8/1997 | Issa .................... A61B 18/1206 606/41 |
| 6,032,673 | A | * | 3/2000 | Savage ............... A61B 18/1485 128/898 |
| 6,491,690 | B1 | * | 12/2002 | Goble .................. A61B 18/148 604/22 |
| 7,465,302 | B2 | | 12/2008 | Odell et al. |
| 8,333,760 | B2 | * | 12/2012 | Roggan ............... A61B 18/1233 606/32 |
| 2012/0179072 | A1 | | 7/2012 | Kegreiss |

* cited by examiner

ELECTROSURGICAL DEVICE AND ITS USE FOR REMOVING LARGE BLADDER TUMORS

CROSS-REFERENCE TO RELATED APPLICATIONS

This application is a 371 of International Application No. PCT/IB2012/002145, filed Oct. 25, 2012, the disclosure of which is expressly incorporated herein by reference in its entirety.

The present invention relates to a device for performing surgery. Being a PCT application, for those countries where appropriate, the present invention also relates to a method of performing surgery itself.

In Onco-Urology, a situation may be encountered where a tumor resides in the bladder of a patient. It may be necessary to remove this tumor for therapeutical or diagnostical purposes. In this case, it is preferred to do so using minimally invasive surgical treatment.

Specifically, superficial bladder tumors and superficial muscle-invasive tumors should be treated using a transurethral resection technique. At the same time, transurethral resection of bladder tumor, TURBT, serves as a diagnostic procedure to assess the histopathological type and stage of the disease and can be performed for palliative and haemostatic purposes.

Three electric TURBT techniques are currently in use, the choice depending on the tumor size and location, compare R. Hofmann, "Endoskopische Urologie Atlas and Lehrbuch", Springer Verlag, 1. Auflage 2005, p. 124-133. Known transurethral resection techniques include laser and electric vaporization of bladder tumors, as well as high-frequency current-based TURBT.

However, laser and electric vaporization of bladder tumors are not in wide use per se, as they do not provide means for obtaining pathology sampling material, which prevents accurate diagnosis essential for choosing adequate post-operative treatment appropriate medical supervision protocol. Thus, high-frequency current-based TURBT is often preferred.

In as far as traditional resection by parts or removal en bloc is done by HF transurethral resection, the HF current based transurethral resection procedure requires an optical resectoscope with a video system, an angular (90°) active HF-resection loop electrode and high-frequency current (electric resection). Continuous or cyclic bladder perfusion with sterile conductive solution is required throughout the whole resection procedure. The degree of bladder filling and correspondingly the bladder wall thickness are controlled by perfusion rate.

There exist high-frequency electrosurgical devices intended for dissection and coagulation equipped with means for automatic regulation of the high frequency voltage, means for automatic regulation of the voltaic arc intensity and means for automatic regulation of the peak power—the PPS (Power Peak System)—during the operation with the apparatus electrode being used in an aqueous medium, for instance in the process of transurethral resection of the urinary bladder tumor. It should be noted that where reference is made to manually setting of these parameters in this disclosure automatic and/or automatic subsequent control is considered to be encompassed as well.

Using these devices according to the known art, small tumors—and only those—can be removed by horizontal resection. The tumor is resected layer-by-layer, starting from its top to its base. This technique is unacceptable for highly vascular tumors, as it causes excessive tissue bleeding, which considerably impairs visualization in the course of the operation.

Reference is made to the TURBT technique as stipulated by Russian patent #2417775 published on May 10, 2011, which is fully incorporated herein by way of reference and is also considered the closest prior art to the technique described herein. The known method involves en bloc resection of bladder tumors less than 1 cm in size with a single backward motion of the loop electrode, supporting the resected tissue by the branches of the frame end of the loop and subsequent evacuation of the tissue fragments via the resectoscope tube.

The drawback of this technique is its limitation with respect to the size of the tumors. It is not possible to en bloc remove bladder tumors regardless of their size, location and the degree of bladder wall invasion. Therefore, things stand differently with large (more than 4 cm in diameter) tumors infiltrating the muscle layer of the bladder wall. In the overwhelming majority of cases conventional TUR of such tumors is not radical and patients often have to face cystectomy.

Therefore, in case of bladder malignancy, the conventional TUR techniques have certain disadvantages and limitations, namely violation of the ablastics principle (that is, the tumor is removed by fragmentation without its nutrient vessels being defunctioned), which may result in tumor dissemination or early relapse. A further disadvantage is enhanced tumor tissue bleeding, impairing visualization during the operation. Furthermore, there is an increased risk of bladder wall perforation as in the process of resection the loop is being advanced deep in the tissues, i.e. outside visual control. Also, when the tumor is located on the lateral bladder wall, TURBT is practically unfeasible without prior endotracheal anesthesia and muscular relaxation due to the risk of operation-induced obturator nerve syndrome; Finally, TUR of highly vascularized large tumors requires prolonged high-flow perfusion with sterile solution to secure constant visual control of the bladder wall and the residual tumor, which is jeopardized by excessive tissue bleeding. This, in turn, considerably elevates the intravesical pressure and consequently enhances the risk of bladder wall perforation and extravasation of urine.

Thus, while there exist techniques and instruments for the removal of tumors that are small, that is tumors of up to 1 cm in diameter, and superficial within the bladder mucosa, the idea to remove bladder tumors en bloc has been challenging the world urological community for decades.

It would be helpful to allow for better treatment of patients having bladder tumors. In particular, it would be helpful to facilitate a tumor removal procedure for a surgeon treating a patient having a large bladder tumor.

The object of the present invention is to provide novelties having an industrial applicability.

It will be seen hereinafter that using a novel surgical method, vertical or radial resection can be used for removal of large tumors, including solid bladder tumors. It is noted that applicant reserves the right to claim this new and inventive medical method for those countries where applicable.

To perform the new method of surgery, improved electrosurgical devices will be disclosed. However, before describing this new electrosurgical device, it is believed that for a better understanding of the advantages of the new device, the surgical method it is intended for should be described.

The medical treatment to be carried out using the present invention will be in compliance with the principle of ablastics. By preservation of anatomy structures in the course of TURB it is possible to eradicate the bladder tumor en bloc regardless of its size, location and the degree of bladder wall invasion.

According to the surgical procedure disclosed here, a way out of the problem of removing large tumors has been found by analyzing and taking into account the peculiarities of the bladder wall anatomy. The bladder wall has an overall thickness of 4-5 mm and it consists of several layers, namely, mucosa, submucosa, inner, middle and outer muscle layers and adventitious membrane. The most important thing here is that all the layers adhere to each other rather loosely and can move along each other within certain limits, which provides for continuous alteration of the two physiological processes: filling up and emptying of the urinary bladder with constant changes of its volume.

This anatomical structure is taken advantage of according to the new method described in isolating the tumor-invaded layers of the bladder wall en bloc within a certain site and separating them from the intact layers (more or less like one peels off layer after layer of an onion) without allowing perforation or rupture of the bladder.

Given this, during the course of the surgical procedure suggested, short turn-on pulses of a monopolar dissection mode can be used for the preparation of the tumor-invaded bladder wall.

Figure 2:
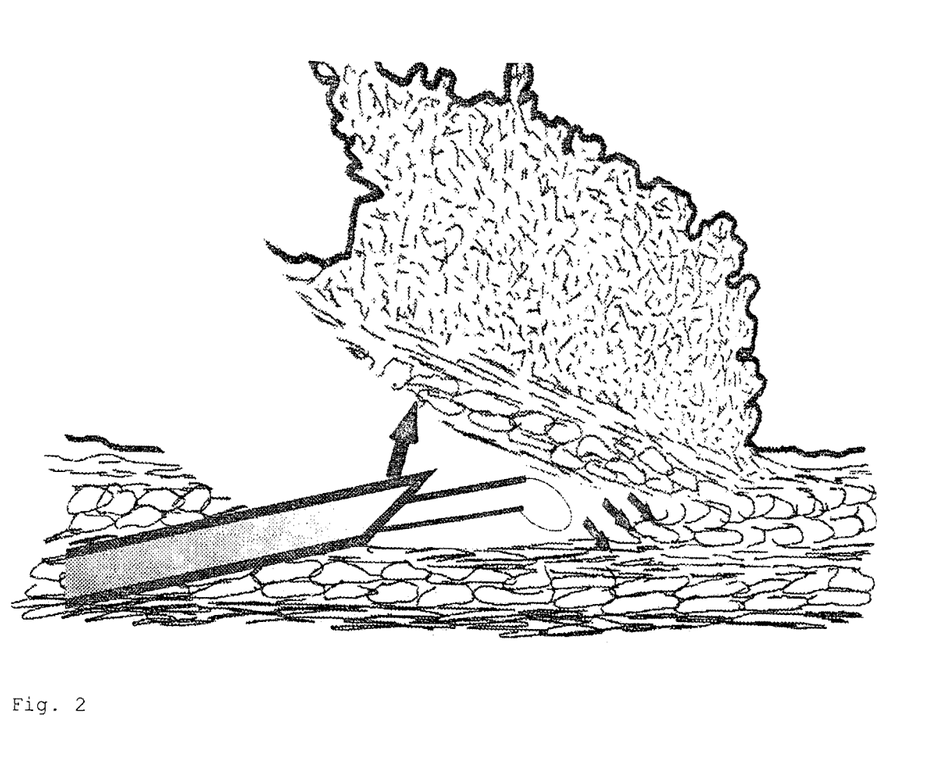
FIG. 2 an illustration of the surgical intervention carried out with the electrode of the apparatus of FIG. 1.

More particularly, the goal set for the TURBT technique including exploration of the bladder and the en bloc radical removal of a tumor using a resection electrode loop of an optic resectoscope is achieved via careful preparation of the bladder wall layers below the tumor base within the intact tissue margin. This is done using step-by-step coagulation and dissection of the tumor nutrient vessels and of the interlayer tissue fibers performed by impulsive turns-on of the electrosurgical apparatus in-use in the monopolar dissection mode. After that, the prepared tissues are shifted off by short motions of the cool resection loop, while the tip of the resectoscope tube is supporting them (cmp. FIG. 2).

In more detail, it is suggested that the resection be performed starting from the intact bladder wall at the tumor base until the outer muscular layer is reached.

For this, a resectoscope is inserted under the tumor base into the space between the layers of the wall as necessary depending on the depth of tumor invasion of the bladder wall, the insertion being such that there are no visual signs of the tumor.

Then, advancing towards the tumor, step-by-step removal of subsequent sections of its tissue sectors is performed strictly downright in the sagittal plane until the previous level of resection is reached. Numerous damaged vessels along the resection margin are coagulated from time to time as practical and necessary. During the course of the surgical intervention, single exophytic papillary tumors of small size (less than 1 cm in diameter) can also be resected with one loop motion performed at the tumor base provided the bladder submucosa is captured by the loop. In all of the above listed techniques the loop in the process of resection is being pulled on and embedded into the layer of the resected tissue with simultaneous turning on of the electrosurgical apparatus in use for rather prolonged interval, i.e. typically more than 2 seconds in the monopolar dissection mode.

Thus, according to the method suggested here bladder tumors can be removed en bloc as a whole with the surrounding intact bladder wall. The method is advantageous in that during the course of the operation only small interlayer tissue fibers and the main vessels running to the tumor have to be dissected. Prior to dissecting the blood vessels they are coagulated using a forced coagulation mode (FORCED COAG) of an electrosurgical device. This mode is used to prevent hemorrhage; when this mode is turned on, the tissues are not dissected but rather sealed as the temperature runs very high at the point of its contact with the loop electrode. This mode can also be used in form of interrupted pulses; however in this case this is not essential. The main parameters of this mode can e.g. be as follows: HF-voltage being pulse-modulated alternating voltage with a nominal frequency of 1 MHz. and a maximal peak value of up to 2600 V, the nominal HF power being 120 watt. The experienced surgeon will know how and when these values can or should be altered. Following this, it has been found both sufficient and preferable to turn on the monopolar resection mode for only a very short instant, typically a split second.

By doing so, the process of mobilizing the tumor becomes short, practically bloodless and safe for the remaining intact bladder wall not invaded by the tumor.

The suggested new surgical method has several major advantages, in comparison with the conventional techniques. In particular, the ablastics principle is observed, that is, the malignant tumor is removed en bloc with surrounding and underlying tissues, and its morcellation is performed no sooner than the nutrient vessels have completely been cut off. Furthermore, preventive coagulation of the major nutrient vessels located inside the bladder wall accounts for minimum tissue bleeding in the course of the operation. Then, the risk of bladder wall perforation is minimized owing to complete visual control of the active electrode movements in the course of the resection. Also, even when large tumors located on lateral walls of the bladder side walls (within the projection of the obturator nerve) are being removed, indications for endotracheal anesthesia with complete muscle relaxation still do not present themselves. In addition, TUR is performed at low-flow perfusion, which reduces the risk of bladder wall perforation and of extravasation of urine, and also saves considerable amounts of the perfusate.

While the procedure can be done by pressing a turn-on pedal of a HF current generator very frequently and briefly in the abovementioned mode, this requires substantive skill and is stressful to the surgeon. So, though it is possible to learn to regulate the length of the turn-on pulses of the resection mode by means of varying the frequency of pressing the foot pedal of the apparatus, very much like the skill of Russian tap-dance can be mastered, this will require time and most probably—special training in a clinical institution with experience in using this technique.

To allow a more easy way to perform the new method of surgery, it is now suggested to modify the HF current generator such that application of the HF energy becomes easier.

For this suggested new surgical method, an electrosurgical apparatus is disclosed having a HF power source providing HF energy for electrosurgery and a circuitry to control the application of said HF energy to an electrode end used in electrosurgically operating on a patient, wherein the circuitry is adapted to apply, when in a dissecting mode, said HF energy for dissecting to an electrode end automatically in the form of pulses such that the pulses automatically have a defined length.

It has been understood that a device having a circuitry that will automatically produce pulses allows to ensure in a very simple way that it is enough to just turn on the monopolar resection mode without the need for special skills other than that of an otherwise experienced surgeon. Using such a device, the process of mobilizing the tumor becomes short, practically bloodless and safe for the remaining intact bladder wall not invaded by the tumor.

None of the other functionalities of a known apparatus needs to be changed. So, every surgeon-urologist will be able to adjust the operation mode of the HF current generator of the present invention according to the tumor spread and his personal experience, which will provide him with an opportunity to perform the surgical intervention safely and with invariably perfect result. Therefore, while it is of course possible to learn to regulate the length of the turn-on pulses of the resection mode by means of varying the frequency of pressing the foot pedal of the apparatus (just as the inventor did), there is no more need for the difficult practice that was not easier than mastering the skill of Russian tap-dance and has required time and—most probably—special training in a clinical institution with experience in using this technique.

It will be obvious that the apparatus disclosed is particularly useful for bladder tumor removal.

Depending on the intended use, and in particular for removal of bladder tumors, the apparatus according to the present invention may in a preferred embodiment further comprise means for continuous or cyclic low-flow bladder perfusion with sterile conductive solution during the course of the operation without overfilling the bladder beyond its physiological volume.

It is advantageous if the electrode to which said HF energy is applied is an active resection electrode loop with 0-45° angle of bending.

Also, in a preferred embodiment the apparatus may be further provided with an optic resectoscope as known per se allowing for visual control of the operation site, preferably at minimal possible focus distance.

It will be understood that a system for surgical intervention according to the present invention will be preferably adapted for use with a rotary tissue morcellator.

Preferably, in the apparatus according to the present invention one of the previous claims wherein the circuitry is adapted to automatically apply in the dissecting mode said HF energy in the form of pulses to said electrode end for lengths of pulses between 0.1 to 2 seconds.

Preferably, in the apparatus according to the present invention a means for selecting a length of automatically generated HF pulses in the dissecting mode is provided, said means preferably allowing for a selection of the length of pulses between 0.1 to 2 seconds and/or wherein the duration of pulses is selectable between 0.1 and 1 second. Using pulses up to 2 seconds will allow the use of lower power and/or treatment of larger areas and/or with larger electrodes, while using very short pulses allow treatment of minute structures. Further reducing pulse lengths will normally not be advantageous in adult patients and will thus be not preferred.

It should be noted that it is possible to use a single shot activation for the circuitry, thus applying one pulse of HF energy to the electrode per activation, thus e.g. triggering one pulse every time a manual or foot switch is depressed while not allowing for a further triggering prior to the release of the switch and the repressing of the switch.

However, it is also possible as an alternative and/or in addition to the one-shot mode to allow for other modes of activation. For example, it would be possible to produce pulse sequences with a given, preferably adjustable pulse repetition rate for as long as a switch is depressed, e.g. a number of e.g. up to 3 or 5 or 10 pulses per interval of e.g. 5-10 secs. for as long as a foot pedal or the like is being continuously pressed. This allows for slow movement of the resection electrode through an area where e.g. coagulation of a number of vessels is necessary and/or when a recession needs to be effected particularly slowly.

Also, it would be possible to apply a burst with a selectable overall maximum number of pulses, again preferably with a given, preferably adjustable repetition rate, the maximum number of pulses in such a burst not being exceeded even if a switch such as a manual or foot switch is depressed for a long period. Also, the repetition rate and/or the energy of a pulse and/or the length of the automatically generated pulses could be made dependent on the strength with which a pedal switch or the like is stepped upon or manually depressed.

It is noted that a large number of possibilities exist to implement circuitries that provide this functionalities. In particular, these functionalities can be implemented with both analog and/or digital electronics.

Preferably, in the apparatus according to the present invention HF energy in the dissecting mode provided to the electrode is provided as monopolar energy for dissection.

Preferably, in the apparatus according to the present invention the HF energy in the dissecting mode is provided as monopolar energy for dissection with a frequency between 300 and 450 kHz. If the current frequency exceeds 450 kHz not only would special equipment be required but also an effect called tissue evaporation effect would be manifested. While there exist special surgical techniques based on this effect, they are seldom practiced because of pronounced electric damage inflicted upon normal tissues adjacent to the tumor in the course of the intervention. Thus, it is preferred for the present invention to have a HF energy with a frequency lower than 450 kHz. For instance, it has been found that a HF current generator BOWA ARC 300 made in Germany having an output current frequency of 330 kHz can be used for performing the new surgical method without the new apparatus of the present invention.

It is considered sufficient and thus preferable if the apparatus according to the present invention supplies a maximal output power for monopolar dissection of 300 watt, the output power preferably being adjustable.

Furthermore, in the apparatus according to the present invention the HF-voltage in the dissecting mode preferably is an unmodulated sinusoidal alternating voltage. It is also preferable if the maximal HF-voltage in the dissecting mode is below 600 V, preferably equal to or below 570 V.

Also, in a particular preferred embodiment, in the apparatus according to the present invention the circuitry is further adapted to apply HF energy for blood vessel coagulation having a nominal frequency of >500 kHz, preferably 800-1500 kHz, and a HF power of less than 200 watt. A typical and thus preferred HF frequency will be 1 MHz. This mode allows to prevent hemorrhage. When this mode is turned on, the tissues are not dissected but more like sealed as the temperature runs very high at the point of its contact with the loop electrode. This mode can also be used in form of interrupted pulses as it has been described above pertaining to the monopolar dissection mode; however, in this case, this is not essential. In a practical embodiment, main parameters of this mode as follows have been found to be applicable; however, it is noted that these parameters are not intended to be restricting or limiting the scope of the invention and that a sufficiently experienced surgeon will know how and when to use values different from these: a pulse-modulated alternating HF voltage with a nominal HF frequency of 1 MHz, a maximal peak value of up to 2600 V and a nominal HF power of 120 watt. In this way, prior to dissecting, the blood vessels can be coagulated using forced coagulation mode more easily.

It should be noted that the electrosurgical apparatus can and preferably will make use of (at least) two controllers at the output of the HF current, one controller supporting the monopolar dissection and one controller the coagulation mode. It has been stated above for the monopolar dissection controller that preferably the length of the automatic turn-on pulse(s) and e.g. the length of the interval between the pulses should be controlled. It should be noted that in a particular preferred embodiment corresponding adjustments will be possible for the coagulation mode as well. These at least two controllers can help to keep the needed parameters within given diapasons without particular effort for the surgeon.

The electrosurgical device of the invention will not require to change or give up other main features of known electrosurgical devices, such as safety measures, combination of the patient end with optical instruments, light asf. Yet, every surgeon-urologist will still be able to easily adjust the operation mode of the HF current generator according to the tumor spread and his personal experience, which will provide him with an opportunity to perform the surgical intervention safely and with invariably perfect result.

The present invention will now be described without restriction to the particular embodiment and thus by way of example only, referring to the drawing. What is shown in the drawing is FIG. 1 the electrosurgical device according to the invention.

Figure 1:
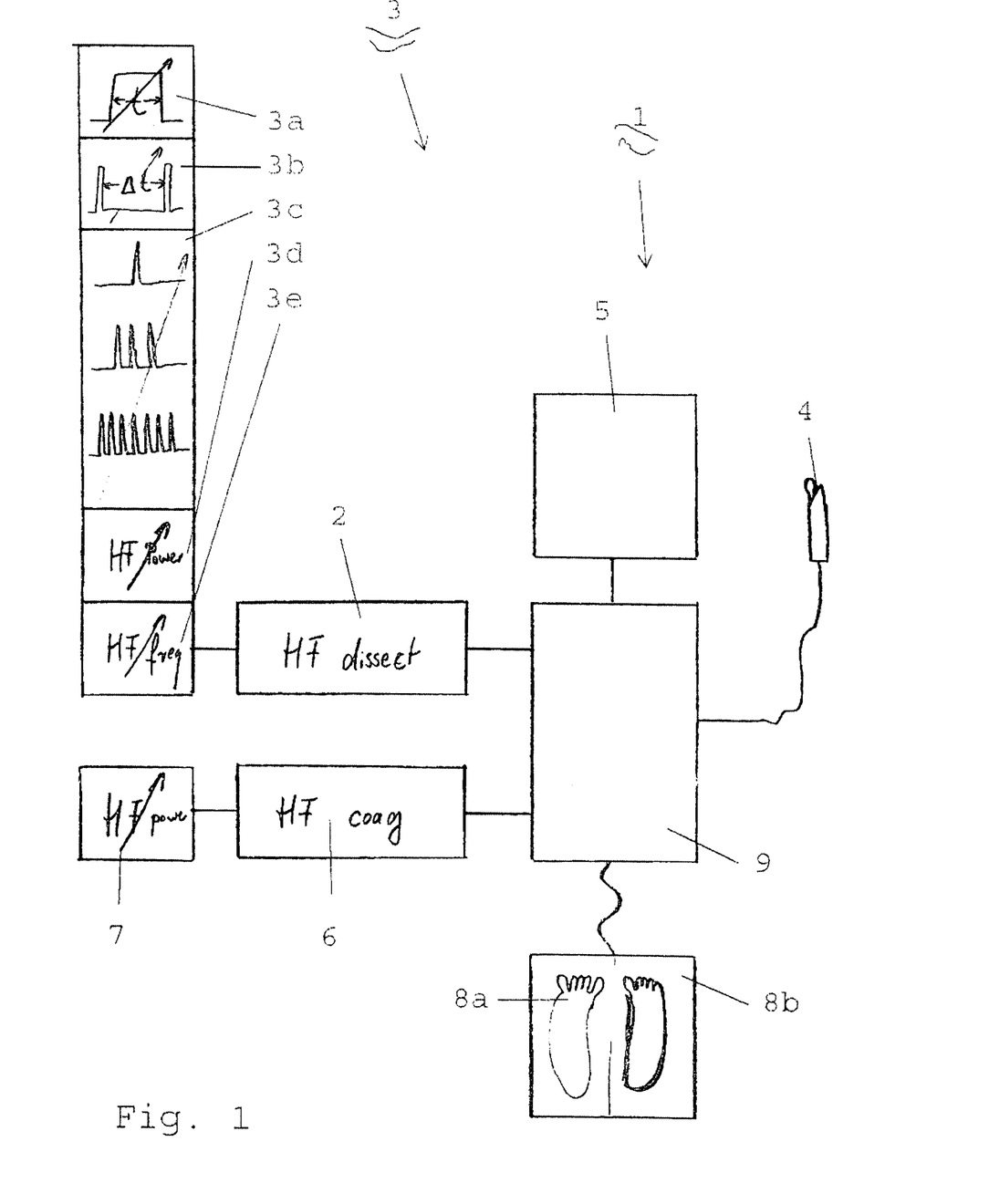

According to FIG. 1, an electrosurgical apparatus 1 has a HF power source 2 providing HF energy for a dissecting step during electrosurgery and a circuitry 3 to control application of said HF energy to an electrode end 4 used in electrosurgically operating on a patient. In this electrosurgical apparatus 1 the circuitry 3 is adapted to apply in a dissecting mode said HF energy for dissecting to an electrode end 4 automatically in the form of pulses such that the pulses automatically have a defined length.

The electrosurgical apparatus 1 is, other than with respect to the circuitry and devices described herein, conventional as known per se and adapted for bladder surgery in a manner known per se to the skilled person. To this end, the electrode end 4 is part of a surgical intervention end which is a resectoscope built in a per se conventional manner and allowing to view the operation site during the surgery. It also is adapted for continuous or cyclic low-flow bladder perfusion with sterile conductive solution and/or of spinal anesthesia. Corresponding controls are provided, cmp. reference sign 5. The electrode 4 itself is preferably built as a loop electrode having an appropriate angle.

The control circuit 3 is adapted to set a pulse length t per pulse as indicated by arrow 3a; to further set a repetition rate (or time interval between pulses) as indicated by arrow 3b; to select between a single shot mode, a burst mode and a mode of repetition of pulses for an infinite time as long as an activation signal is received, as indicated by arrow 3c; the HF output power as indicated by arrow 3d; and the HF frequency for dissection as indicated by arrow 3e.

The electrosurgical apparatus 1 is further provided with a HF power source for coagulation 6 having an output power which can be set via a control 7 as indicated by the arrow in box 7. A selection as to whether HF power from the coagulation power source or the dissection power source is to be thru-connected to the electrode end 4 can be made using a foot pedal 8 having two areas for activating either one (and only one at a time) of the power sources. For the sake of completeness, it should be noted that the coagulation power source and dissection power source need not necessarily be distinct; instead, it would be feasible to operate the same power source in different manners so as to either provide energy for dissection or for coagulation.

The electrosurgical apparatus 1 is further provided with a foot pedal switch 8 having a number of different pedals, here two pedals 8a and 8b. Stepping on pedal 8a, the pulse or pulses from the HF dissect power section 2 are thru-connected to electrode 4 in an interface 9. These pulses are generated as per the adjustment using controls 3a-3e and they thus have appropriate power, frequency, length, repetition rate and are in one of single shot mode, burst mode or continuous pulse generation mode as selected. Stepping on pedal 8b, the coagulation power set by control 6 will be applied to electrode 4. A control detects if both pedals are activated simultaneously. In that case a warning signal is generated but no electrical power is applied to electrode 4.

The device according to the present invention is useful in a surgical procedure carried out as follows:

The goal set for the TURBT technique which includes exploration of the bladder and en bloc radical removal of the tumor using the active resection electrode loop of the optic resectoscope with active resection loop electrode is achieved via careful preparation of the bladder wall layers below the tumor base within the intact tissue margin.

At that by step-by-step coagulation and dissection of the tumor nutrient vessels and of the interlayer tissue fibers is performed by impulsive turns-on of the electrosurgical apparatus in-use in the monopolar dissection mode. After that the prepared tissues are shifted off by short motions of the cool resection loop, while the tip of the resectoscope tube is supporting them. The duration of each turn-on impulse of the electrosurgical apparatus in-use operating in the monopolar dissection mode is set in such a manner using the circuitry 3 as to not exceed one second per pulse.

Using the device according to the present invention, there is no need for the surgeon to constantly control the duration and frequency of the pulses switching on the resection mode of the high-frequency electrosurgical apparatus by means of modifying frequency and time of pressing the foot pedal of an electrosurgical device used in the process of bladder wall preparation and tumor removal. Instead, the relevant parameters can be set in advance and then the surgical apparatus can simply be triggered using the pedal 8.

Using the suggested operation mode of the high-frequency electrosurgical apparatus of the present invention thus makes it possible for any urologist even with limited experience of transurethral interventions to remove urinary bladder tumors en bloc safely and radically regardless of their location, size or the depth of bladder wall invasion.

Preliminary coagulation of the bladder mucosa and of the vessels passing through the mucosa around the tumor base is carried out as recommended specifically with subsequent dissection of the bladder wall deep down to the external muscle layer along the outline drawn by coagulation process, preferably not farther than 1.5 cm from the tumor base depending on the size of the focus.

The dissection will be performed by impulse turns-on of the electrosurgical apparatus in-use operating in the monopolar dissection mode. This method employs use of the standard active resection electrode loop (with 0-45° angle of bending) and operation at minimal possible focus distance of the optical resectoscope. This method allows use of continuous or cyclic low-flow bladder perfusion with sterile conductive solution and of spinal anesthesia instead of general anesthesia with muscle relaxation.

This method is performed in the following sequence of its steps. The alleged method of TURBT requires use of optical resectoscope with video system, standard active HF-resection electrode loop with 0-45° angle of bending and high-frequency current (electric resection). During the resection procedure, continuous or cyclic bladder perfusion with sterile conductive solution must be arranged. Due to secure bleeding control, low-flow perfusion can be used. After exploration of the bladder coagulation of the bladder mucosa and of its vessels around the visible tumor base at the distance not farther than 1.5 cm from it depending on the size of the focus. At the next step, the mucosa, the submucosa and the internal muscle layer are dissected in the previously coagulated area.

The prepared tissues are easily shifted off by the resection loop; light tension created by the latter being enough as bladder wall layers are rather loosely bound to each other. This is shown in FIG. 2.

From this step on, the surgeon will watch out to prevent over-filling the bladder with the operating solution. Meanwhile, the tip of the resectoscope tube is advanced into the defect now having appeared in the bladder wall and slight traction is applied to the prepared tissues en bloc in the direction of the resection. At this stage, the margin of the tumor or inflammatory infiltration of the bladder wall can be clearly seen, which immediately accounts for the choice of the layer for further preparation. The layer of preparation depends on tumor expansion and the depth of its invasion. Mild pulling is usually enough to split the tissues within the working layer but for the blood vessels coming closely to the tumor and separate muscle fibers intertwined between the external and internal muscle layers.

These elements are coagulated step-by-step and dissected with the resection loop by impulses automatically generated when the pedals 8a or 8b respectively are stepped upon. The electrosurgical apparatus, when operating in the monopolar dissection mode, will be set so that the impulse duration does not exceed one second. On the one hand, this allows easy bleeding control in the course of the operation as the main nutrient vessels of the tumor are coagulated and dissected upstream their division into smaller branches.

On the other hand, even without drug-induced muscle relaxation, the patient does not suffer from the clinically significant obturator nerve syndrome and concomitant complications. Besides the suggested short-pulse switching-on of the resection mode precludes significant rectification of the part of the high-frequency alternating current, which otherwise occurs due to the voltaic arc springing up between the active electrode and the tissue in the process of dissection, which, in turn, minimizes formation of the more or less heavily modulated components of the current capable of causing marked irritation of such irritation-susceptible tissues as nerves and muscles.

Clinical significance of this effect lies in the fact that pulsed switching-on of the high-frequency electrosurgical apparatus operating in the resection mode in the course of transurethral resection of urinary bladder tumor with the above described technique in use might cause only minimal stimulation of the obturator nerve manifesting in just minor jerks of the ipsilateral lower extremity but completely precluding possible bladder wall perforation.

Owing to this effect the intervention can in all cases, regardless of the tumor size or location, be performed under spinal anesthesia, which is particularly important in elderly and weak patients.

As the surgeon advances deeper under the tumor base he at the same time performs step-by-step coagulation and dissection of the mucosa and submucosa on both sides of the tumor along the previously outlined resection margin until the resected tissues are completely separated en bloc from the bladder wall. The elaborated technique makes it possible to perform resection under complete visual control throughout the whole operation. Practically complete absence of tissue bleeding in the course of the entire operation, step-by-step tissue dissection only at margin of the contact with the resection loop, as well as operation at small focus distance (with minimal loop extension) contribute to it.

The new surgical method the electrosurgical device is intended for a large number of patients. This is documented by way of example with reference to the following cases. Then case histories below illustrate the feasibility of the new technique and the achievement of the set goals.

Case 1

Patient Y., aged 78, was admitted to the Department of Oncosurgery III of Minsk Municipal Health Center for Clinical Oncology (MMHC-CO) for complaints of obstructed urine flow and occasional hematuria with clots in the course of the last 3 months. The patient's state upon admission was satisfactory, he was fully conscious, with normal color of the skin, without edema or enlargement of peripheral lymphatic nodes. His hemodynamic parameters were within normal limits, blood pressure 130/80 mm/Hg. No palpable masses detected upon physical examination. The patient had trouble voiding and blood could be traced in his urine with naked eye.

The examination and laboratory test results were as follows:

ECG: sinus rhythm, HR—76 bpm, the electric axis of the heart in the normal position. Thorax X-ray exam: residual post-tuberculosis changes, emphysema, and pneumosclerosis.

Abdominal ultrasound findings: unremarkable, no metastases found.

The kidneys: unremarkable. The bladder contained 200 ml of urine; a hyperechogenic tissue mass 55×47 mm in size was detected on the left bladder wall. The prostate was not enlarged, 32×35×33 mm in size. Radionuclide renographic study: secretory and excretory function of the right kidney considerably impaired; markedly compromised secretory and excretory function of the left kidney (parenchymal type of the curve). 8 Hemogram: RBC—$3.36 \times 10^{12}$, HG—99 g/l, color index—0.88, PLT—$305 \times 10^{12}$, WBC—$4.8 \times 109$, eosinophil cells—1%, stabs—2%, segmented neutrophil cells—69%, lymphocytes—19%, monocytes—9%, ESR—36 mm/h. Biochemical blood test: total protein—80.1 g/l, urea—5.6 □mol/l, total bilirubin—9.0 □mol/l, glucose—4.7 □mol/l. Urinalysis: reddish, muddy, specific gravity—1010, alkaline reaction, protein content 1.05 g/l, RBC cover all fields of vision.

The patient was scheduled for an operation. Under spinal anesthesia the 24 CH resectoscope tube was easily passed through the urethra. Under visual control, the resectoscope was introduced into the bladder. The bladder capacity was 400 ml. Exploration revealed that the prostate was not enlarged. The mucosa was of trabecular built with patchy inflammatory foci and marked vascular injection throughout. Both ureter orifices were unremarkable. A villous-solid mass 55 mm in diameter on a wide base was located on the left lateral wall passing over to the posterior wall of the bladder. The tumor was continuously bleeding. The bladder cavity was rinsed to remove approximately 30 ml of fresh and old blood clots. No other pathological changes were revealed. The en bloc resection of the left lateral and posterior bladder wall with the tumor was performed using precision electric thermal preparation deep down to the external muscle layer. Bleeding control was secure throughout the operation. The bladder wall integrity was checked. The resected piece of tissue was fragmented in the bladder cavity for subsequent evacuation. The bladder cavity was rinsed to remove the resected tissue fragments. Biopsy of the resection margin and residual bleeding check was performed. Urethral Foley catheter CH 20 was placed into the bladder for urine diversion. Upon bimanual palpation bladder felt soft, without palpable masses. The prostate felt atrophic, of elastic consistency. Macro-preparation: 1. Tumor of small-villous structure, 5.5 cm in diameter, with the base and surrounding mucous tissue, fragmented. 2. Resection margin sample. 9 Pathology report #2009/41114-214: papillary transitional cell carcinoma with invasion of the subepithelial connective tissue, pT1G2, surgical margin negative for tumor growth. The post-operative period was uneventful. The catheter was removed on the 2nd day after the operation. Normal voiding was restored. Hemogram: RBC—$4.18\times10^{12}$, HG—123 g/l, color index—0.82, PLT—$275\times10^{12}$, WBC—$8.4\times109$, eosinophils—1%, stabs—3%, segmented neutr.—72%, lymphocytes—11%, monocytes—12%, ESR—41 mm/h. Biochemical blood test: total protein—78.0 g/l, urea—3.8 □mol/l, total bilirubin—9.8 □mol/l, glucose—4.6 □mol/l. Urinalysis: light yellow, slightly muddy, specific gravity—1006, alkaline reaction, protein content—0.075 g/l, pavement epithelium, 1-2 per field of vision; WBC—2-3 per field of vision; RBC—10-18 per field of vision. On the 8th day after the operation the patient was discharged in satisfactory condition, for further supervision by a urologist of the outpatient department with urotropic antimicrobial drugs recommended for oral intake for 10 days. Control examination was recommended after 3 months. Upon post-operation control 3 months later, the patient's state was satisfactory. Urine cytology test negative for tumor cells. Abdominal ultrasound findings: unremarkable, no metastases found. Kidney ultrasonogram: unremarkable. The bladder, contained 200 ml of urine and was round-shaped with distinct even outline. The bladder wall thickness did not exceed 0.4 cm. No additional masses were found. The prostate was not enlarged.

Case 2

Patient K., aged 53, was hospitalized urgently to the Department of Oncosurgery III of Minsk Municipal Health Center for Clinical Oncology (MMHCCO) for complaints of hematuria with clots and obstructed urine flow. The patient's state upon admission was satisfactory, he was fully conscious, with pallid color of the skin, without edema or enlargement of peripheral lymphatic nodes. His hemodynamic parameters were within normal limits, blood pressure 130/80 mm/Hg. No palpable masses detected upon physical examination. The patient had trouble voiding and blood could be traced in his urine with naked eye. The examination and laboratory test results were as follows: ECG: sinus rhythm, HR—88 bpm. Thorax X-ray exam: unremarkable. Abdominal ultrasound findings: unremarkable, no metastases found. The kidneys: unremarkable. The bladder contained 300 ml of urine; a hyperechogenic tissue mass 58×48×42 mm in size on a wide base was detected on the left bladder wall. In the bladder cavity hyperechogenic masses not fixed to the bladder wall (blood clots) were visualized. Enlarged lymph nodes up to 14 mm in diameter were detected along iliac vessels on the left side. The left ureter was dilated up to 0.8 mm in diameter along its entire length. Pelvic computer tomography: CT picture of an invasive tumor of the left bladder wall, metastatic lesion of the iliac lymph nodes on the left side, osteoblastic metastases in the pelvic and sacral bones. Hemogram: RBC—$4.94\times10^{12}$, HG—113 g/l, color index—0.80, PLT—$183\times10^{12}$, WBC—$5.3\times109$, eosinophils—1%, stabs—3%, segmented neutr.—67%, lymphocytes—23%, monocytes—7%, erythrocyte sedimentation rate—20 mm/h. Biochemical blood test: total protein—81.3 g/l, urea—5.9 □mol/l, total bilirubin—14.8 □mol/l, glucose—5.2 □mol/l. Urinalysis: brown color, specific gravity—1017, acid reaction, protein content—0.45 g/l, pavement epithelium, 1-2 per field of vision; leucocytes—3-6 per field of vision; RBC—in large quantity. The patient was taken to operation room for emergency surgical intervention because of increasing macrohematuria. Under spinal anesthesia the 24 CH resectoscope tube was easily passed through the urethra and under visual control the resectoscope was introduced into the bladder. The bladder capacity was 300 ml. Exploration of the bladder revealed slightly enlarged prostate, the bladder cavity contained up to 60 cm3 amount of floating blood clots that were evacuated. The mucosa was of trabecular built with patchy inflammatory foci and marked vascular injection throughout. The right ureter orifice was unremarkable. A smallvillous mass 55 mm in diameter on a wide base involving the left ureter orifice was located on the left lateral wall. The tumor was continuously bleeding. Signs of tumor invasion were detected: multiple dilated and convoluted vessels around the wide tumor base, the latter completely immobile. On the anterior wall of the bladder neck another tumor of similar structure 0.6 cm in diameter on a narrow base was detected. No other pathological changes were revealed. The en bloc resection of the left lateral bladder wall with the tumor was performed using precision electric thermal preparation deep down to the paravesical fat layer. At that the intramural part of the ureter was mobilized and cut 0.8 cm above the visual tumor margin. An Endo-Soft Radiopaque Double Pigtail Stent CH 7.5 by COOK Medical was placed into the left kidney. Bleeding control was secure throughout the operation. The bladder wall integrity was checked. The resected piece of tissue was fragmented in the bladder cavity for subsequent evacuation. The tumor on the anterior was resected. The bladder cavity was rinsed to remove the resected tissue fragments. Biopsy of the resection margin and residual bleeding check was performed. Urethral Foley catheter CH 22 was placed into the bladder for urine diversion. Upon bimanual palpation bladder felt soft and mobile. The prostate felt slightly enlarged, of elastic consistency. Macro-preparation: 1. Tumor of small-villous structure, 5.5 cm in diameter, with the base and surrounding mucous tissue, fragmented. 2. Resection margin sample. Pathology report: transitional cell carcinoma with invasion of the muscle layer, pT2bG2, surgical margin contains fat and muscle tissue negative for tumor growth. The post-operative period was uneventful. The catheter was removed on the 3rd day after the operation. Normal voiding was restored. Hemogram within normal limits; urinalysis: light yellow, slightly muddy, specific gravity—1020, acid reaction, protein content—0.12 g/l, pavement epithelium: 1-2 per field of vision; WBC: 2-4 per field of vision; RBC: 20-40 per field of vision. On the 10th day following the operation the patient was discharged in satisfactory condition, his further treatment protocol including chemotherapy. The patient was scheduled for repeated hospitalization 6 months after the operation. No complaints were presented. The patient's state upon admittance was satisfactory he was fully conscious, with pale pink color of the skin, without edema or enlargement of peripheral lymphatic nodes. His hemodynamic parameters were within normal limits, blood pressure 130/80 mm/Hg. No palpable masses detected upon physical examination. The patient had no trouble voiding and his urine was clear. The examination and laboratory test results were as follows: ECG: sinus bradicardia, HR—65 bpm. Hemogram: RBC—3.40×10$^{12}$, hemoglobin—120 g/l, color index—0.80, platelets—210×10$^{12}$, leukocytes—3.8×109, eosinophils—4%, stabs—4%, segmented neutr.—68%, lymphocytes—22%, monocytes—2%, erythrocyte sedimentation rate—15 mm/h. Total protein—76.6 g/l, urea—5.4 □mol/l, total bilirubin—17.8 □mol/l, glucose—4.9 □mol/l. Urinalysis: light yellow color, transparent, specific gravity—1020, acid reaction, protein—neg., pavement epithelium, 1-2 per field of vision; WBC—6-10 per field of vision; RBC—4-6 per field of vision. Cystoscopy was performed under spinal anesthesia. The 22 CH tube was easily passed through the urethra. The cystoscope was introduced into the bladder under visual control. Mucosa was found to be of normal structure all over, with patchy inflammatory foci. The post-resection scar 2.8× 2.5 mm in size with foci of loose mucosa surrounded by bullous edema can be seen on the left bladder wall adjacent to the bladder neck. The left ureter orifice is patulous, tumor-free and contains the stent. No other pathological formations were revealed in the bladder. Biopsy of the post-resection scar on the left bladder wall was performed. Residual bleeding was checked. The stent was removed using forceps and CH18 urethral catheter was inserted into the urethra. Macro-preparation: Small bladder wall fragments taken from the post-resection scar on the left bladder wall. Pathology report: fragments of fibrous muscular tissue with mild inflammation and residuals of transitional epithelium lining. The post-operative period was uneventful. The catheter was removed on the 1st day following the operation. Normal voiding was restored. Conclusion: the patients' condition is satisfactory. In the first case, the bladder was preserved and the patient voided the natural way. In the second case, complete tumor eradication made it possible to control macrohematuria and deblock the left kidney, which, in turn, provided conditions for full-scale chemotherapy with positive effect. The immediate oncological outcome was good.

What may be considered novel and inventive with, respect to the method of medical surgery in those countries where applicable but what is not expected to be searched subject matter at the time of filing the PCT application is A. TURBT technique
for exploration of the bladder and
en bloc radical removal of a tumor
using the active resection electrode loop of an optic resectoscope
wherein
the bladder wall layers below the tumor base within the intact tissue margin are prepared
using
step-by-step
coagulation and
dissection
of the tumor nutrient vessels and
of the interlayer tissue fibers
performed by impulsive turns-on
of the electrosurgical apparatus
in-use in the monopolar dissection mode.

B. The TURBT technique of A wherein
after the electrosurgical equipment has been applied,
the prepared tissues are shifted off by short motions of a—preferably cool and/or inactive—resection loop,
while the tip of the resectoscope tube is supporting them.

C. The TURBT technique as described in A or B wherein the duration of each turn-on impulse of the electrosurgical apparatus in-use operating in the monopolar dissection mode does not exceed one second.

D. The TURBT technique as described in one of A-C, wherein preliminary coagulation of the bladder mucosa and/or of the vessels passing through the mucosa around the visible tumor base is performed with subsequent dissection of the bladder wall deep down to the external muscle layer along the outline drawn by coagulation process, the dissection being performed by impulse turns-on of the electrosurgical apparatus in-use operating in the monopolar dissection mode.

E. The TURBT technique according to one of A-D wherein preliminary coagulation of the bladder mucosa and dissection of the bladder wall and of the vessels in it is performed not farther than 1.5 cm from the tumor base depending on the size of the focus.

F. The TURBT technique according to one of A-E wherein a standard active resection electrode loop with 0-45° angle of bending is used.

G. The TURBT technique according to one of A-F performed at minimal possible focus distance of the optic resectoscope.

H. The TURBT technique according to one of A-G wherein a continuous or cyclic low-flow bladder perfusion with sterile conductive solution is carried out in the course of the operation without overfilling the bladder beyond its physiological volume.

I. The TURBT technique according to one of A-H wherein radical removal of the tumor en bloc regardless of the tumor size, its location and the depth of bladder wall invasion is effected.

J. The TURBT technique according to one of A-I wherein surgery is performed under spinal anesthesia regardless of the tumor size, its location and the depth of bladder wall invasion, so that the risks of clinically significant obturator nerve syndrome are minimized and general anesthesia with muscle relaxation is not required.

K. The TURBT technique according to one of A-J wherein after the en bloc resected tissue lump is complete separated from the bladder wall, a rotary tissue morcellator is used for evacuation of resected en bloc tissue lump exceeding 5 cm in diameter and wherein tumor fragments are evacuated via the optic resectoscope tube.

The invention claimed is:

1. An electrosurgical bladder tumor removal apparatus comprising:
an HF power source providing HF energy for electrosurgery;
an electrode end configured for electrosurgically operating on a patient and to which said HF energy is supplied, wherein the electrode end is an active resection electrode loop with a 0°-45° angle of bending;
a set of controls having:
a first control switch to supply HF energy in a first mode to the electrode end, wherein the first mode is controlled by a set of controls, and wherein the first mode is a dissection mode;
a second control switch to supply HF energy in a second mode to the electrode end, wherein the second mode is controlled by the set of controls, and wherein the second mode is a coagulation mode;
a control for power, frequency, length, repetition rate,
a first selector to select one of a single shot mode, a burst mode, or a continuous pulse generation mode, and a second selector for selecting a length of automatically generated HF pulses in the first mode, wherein said second selector is operable to accept a selection of a pulse length between 0.1 to 2 seconds;

circuitry to control application of said HF energy to said electrode end in the first mode or the second mode, wherein said circuitry is adapted to provide said HF energy in the first mode or the second mode to said electrode end, and to automatically generate pulses of said HF energy such that the pulses have an automatically controlled length and an automatically controlled repetition rate based on settings of the set of controls, said circuitry being adapted to automatically provide said HF energy, in the first mode, said HF energy in the form of pulses to said electrode end, the pulses having a length between 0.1 and 2 seconds, wherein said circuitry is further adapted to apply, in the second mode, HF energy for blood vessel coagulation having a nominal frequency range of 500-1500 KHz and an HF power of less than 200 watts, the electrosurgical bladder tumor removal apparatus comprising:

an element configured to provide one of continuous or cyclic low-flow bladder perfusion with sterile conductive solution during a course of the operation without overfilling a bladder beyond a physiological volume of the bladder;

an optic resectoscope configured to permit visual control of an operation site; and wherein the electrosurgical bladder tumor removal apparatus is adapted to work in conjunction with a rotary tissue morcellator.

2. The electrosurgical bladder tumor removal apparatus of claim 1, wherein the HF energy in the first mode provided to the electrode end is provided as monopolar energy for dissection.

3. The electrosurgical bladder tumor removal apparatus of claim 2, wherein the HF energy in the first mode provided as monopolar energy for dissection has a frequency between 300 and 450 kHz.

4. The electrosurgical bladder tumor removal apparatus of claim 3, wherein maximal output power for monopolar dissection is 300 watts.

5. The electrosurgical bladder tumor removal apparatus of claim 1, wherein HF-voltage in the first mode is an unmodulated sinusoidal voltage.

6. The electrosurgical bladder tumor removal apparatus of claim 1, wherein the maximum HF-voltage in the first mode is equal to or below 570 V.

* * * * *